United States Patent [19]

Gibby et al.

[11] Patent Number: 5,466,439
[45] Date of Patent: Nov. 14, 1995

[54] POLYMERIC CONTRAST ENHANCING AGENTS FOR MAGNETIC RESONANCE IMAGES

[75] Inventors: Wendell A. Gibby, Mapleton; N. Rao Puttagunta, Provo, both of Utah

[73] Assignee: Magnetic Research, Inc., Provo, Utah

[21] Appl. No.: 272,762

[22] Filed: Jul. 7, 1994

Related U.S. Application Data

[63] Continuation-in-part of Ser. No. 975,607, Nov. 12, 1992, Pat. No. 5,330,743.

[51] Int. Cl.$^6$ .................................................. A61B 5/055
[52] U.S. Cl. ................ 424/9.365; 562/565; 436/173; 534/16; 514/492; 514/502; 514/836; 556/50; 556/55; 556/63; 556/77; 556/105; 556/116; 556/134; 556/148
[58] Field of Search .................. 424/9.365; 562/565, 562/566; 436/173; 128/653.4, 654; 556/50, 55, 63, 77, 105, 116, 134, 148; 514/492, 502, 836; 534/16

[56] References Cited

U.S. PATENT DOCUMENTS

| | | | |
|---|---|---|---|
| 4,880,008 | 11/1989 | Lauffer | 128/654 |
| 5,011,925 | 4/1991 | Rajagopalan | 544/58.1 |
| 5,023,072 | 6/1991 | Cheng | 424/9 |
| 5,057,302 | 10/1991 | Johnson et al. | 424/1.1 |
| 5,138,040 | 8/1992 | Moore et al. | 534/16 |
| 5,155,215 | 10/1992 | Ranney | 534/16 |
| 5,290,537 | 3/1994 | Moore et al. | 424/9 |
| 5,312,617 | 5/1994 | Unger et al. | 424/9 |
| 5,403,576 | 4/1995 | Lin et al. | 424/9 |

*Primary Examiner*—Gary E. Hollinden
*Attorney, Agent, or Firm*—I. Morley Drucker; Howard N. Sommers; Daniel R. Kimbell

[57] ABSTRACT

A polymeric contrast enhancing agent for magnetic resonance images having a chelating agent, which can be bound to metal ions having at least one unpaired electron, such as gadolinium. Examples of such chelating agents include DTPA-ethylenediamide-methacrylate copolymer and poly-(DTPA-ethylenediamide). These contrast enhancing agents, bound to the metal ions, are then administered to a patient, and following this the MR images are taken.

18 Claims, No Drawings

POLYMERIC CONTRAST ENHANCING AGENTS FOR MAGNETIC RESONANCE IMAGES

CROSS REFERENCE TO RELATED APPLICATION

This is a continuation-in-part to U.S. patent appplication Ser. No. 07/975,607, filed Nov. 12, 1992, which issued on Jul. 17, 1994 as U.S. Pat. No. 5,330,743, to Wendell A. Gibby, et al., for "AMINOSACCHARIDE CONTRAST ENHANCING AGENTS FOR MAGNETICS RESONANCE IMAGES."

BACKGROUND OF THE INVENTION

1. Field of the Invention

This invention relates to NMR shift reagents, and in particular, polymer contrast enhancing agents for magnetic resonance imaging, and their use in imaging portions of a patient's body.

2. Brief description of the Prior Art

Magnetic Resonance (hereinafter MR) imaging is one of the newest and least deleterious methods of viewing the interior of the human body. Radio waves interact with protons in a magnetic field to produce images having superior soft-tissue contrast compared to X-ray tomography. However, the technique can be non-specific, that is, it may be impossible to distinguish from between many pathological conditions, such as between cancer and the edema surrounding the cancer, active and inactive multiple sclerosis plaques and bowel from other adjacent organs.

Contrast agents enhance various portions of the MR image by changing, usually decreasing, the relaxation times of the protons in the immediate vicinity to the agent. This allows the area of interest to be much more conspicuous than surrounding tissue. One example of a contrast agent is that disclosed in the European Patent No. 3,302,410 of A.G. Schering for gadolinium diethylene triamine pentaacetic acid complex (hereinafter Gd DTPA). Gd DTPA has been attached to a variety of macromolecules, for example monoclonal antibodies, albumin, lipids and polysaccharides. The structure of DTPA is shown below:

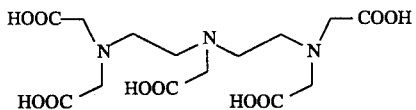

Other agents, such as ethylene diamine tetraacetic acid (hereinafter EDTA), and 1, 4, 7, 10 tetraazacyclododecane, N, N', N", N'"-tetraacetic acid (hereinafter DOTA), have been chelated with Gd in an effort to make a superior contrast agent.

The utility of a specific MRI contrast agent varies depending upon the clinical problem to be addressed and the organ of interest to be imaged. For example, extracellular fluid agents such as gadolinium DTPA, gadolinium DOTA, and gadolinium DTPA BMA (the structure of which is shown further below) work well in organs such as the brain and spinal cord, where the normal brain parenchyma has a barrier to permeability of the contrast agent and pathologic conditions such as cancer do not. However, these contrast agents work poorly for imaging of the vascular system as the majority of the material is lost to the extracellular fluid space. Furthermore, they can at times be deleterious in imaging organs such as the liver and spine in which lesions can be made to appear isointense to normal tissue. They can provoke variable enhancement patterns in organs such as the kidneys in which their high concentration first darkens and then brightens parenchyma. They are poor gut agents because of dilution effects, and poor coating of the bowels.

Some prior art chelates such as gadolinium DOTA and HP-DO3A (the structure of which is shown further below) are cyclic compounds which, although thermodynamically more stable than open chain compounds. However, their synthesis requires a complex, tedious, and expensive process. It would be advantageous for a compound to have improved thermodynamic stability over, say, DTPA or DTPA-BMA, yet not require the expense of ring synthesis.

It would be advantageous in certain conditions (e.g. liver metastasis) for the contrast material to specifically target organ receptors. Examples would be galactose receptors in the lever, polymeric material staying within the blood vessels and heart chambers, or intrathecal administration of a contrast agent with a glucose moiety which might attach to glucose receptors within the brain.

U.S. Pat. No. 4,822,594 to Gibby reports polysaccharide conjugates of Gd DTPA. While these are generally useful compounds, they have an unstable shelf life at neutral pH.

Prior art chelates of Gd, and other paramagnetic metals, suffer from several defects. The body rapidly excretes Gd DTPA, for example. Furthermore, it is not organ specific.

Another problem with known MR enhancing agents is that the proteins that are used to anchor the simple chelates, monoclonal antibodies and the like, may provoke allergic reactions in the recipient. Furthermore, proteins are expensive and carry risks of viral pathogens.

U.S. Pat. No. 4,647,447 to Gries et al. discloses a NMR diagnostic medium containing a well tolerated complex salt formed from the anion of a complexing acid and one or more metal ions. Gries et al. discloses that the complexing acid can be conjugated with biomolecules that are known to concentrate in the organ or part of the organ to be examined. The biomolecules of Gries et al. include insulin, prostaglandins, steroid hormones, amino sugars, peptides, proteins and lipids. Gries et al. includes broad claims to a method of imaging body tissue in a patient by NMR tomography by administering to the patient an effective amount of a pharmaceutical agent comprising an amount, effective to affect such relaxation times, of a paramagnetic, physiologically compatible salt of a physiologically compatible chelate complex of an ion of a lanthanide element of atomic numbers 57–70, or of a transition metal of atomic numbers 21–29, 42, or 44 (Claim 24 thereof) and by administering to the patient an effective amount of a pharmaceutical agent comprising an amount, effective to affect such relaxation times, of a paramagnetic, physiologically compatible salt of a complex of an ion and, as a ligand, an acyclic or cyclic complexing agent containing organic nitrogen, phosphorus, oxygen or sulfur, the complexed ion being an ion of a lanthanide element of atomic numbers 57–70, or of a transition metal of atomic numbers 21–29, 42, or 44 (Claim 65). However, Gries et al. does not disclose any polyamides of DTPA.

Patent Corporation Treaty Application No. WO 90/03804, to Cacheris, et al. discloses metal chelate compositions of monomeric DTPA-bisamides, of the formula:

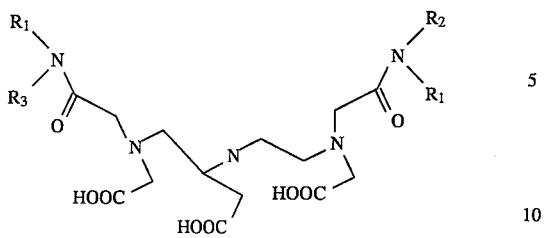

wherein $R_1$ to $R_3$ are each, independently, hydrogen, lower hydroxy (e. g. el. $C_{1-6}$) alkyl, hydroxy lower alkyl, or polyhydroxy ($C_{1-18}$) alkyl.

U.S. Pat. No. 5,077,037 to Wallace discloses magnetic resonance imaging agents including monomeric, mono or polyhydroxy alkylamides of DTPA.

U.S. Pat. No. 5,087,440 to Cacheris, et al. discloses monomeric DTPA bisamides containing heterocyclic and hydroxyalkyl ($C_{1-6}$) amines.

U.S. Pat. No. 5,155,215 to Ranney discloses dextran conjugated Gd-DTPA microspheres, which involve ester linkages.

It would be advantageous to have MR contrast enhancing agents that are organ specific, non-ionic and hydrophilic, do not provoke allergic reactions in the recipient, are not expensive to synthesize, yet are thermodynamically stable and retain better chemical stability.

SUMMARY OF THE INVENTION

An aspect of this invention are compositions of matter comprising polymer chelating agents represented below:

I. A magnetic resonance contrast enhancing agent comprising a chelating agent represented by the formula:

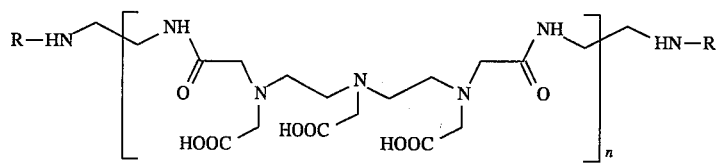

where $n \geq 2$, and R is selected from the group consisting of a polyamide co-polymer of an aminopolycarboxylate and diamine. The polyamide co-polymers of an aminopolycarboxylate includes compounds such as EDTA, DTPA and TTHA (triethylenetetraminehexaacetate), and the diamine includes compounds such as ethylenediamine, propylenediamine, and 1,3-diaminopropane.

II. A magnetic resonance contrast enhancing agent comprising a chelating agent represented by the formula:

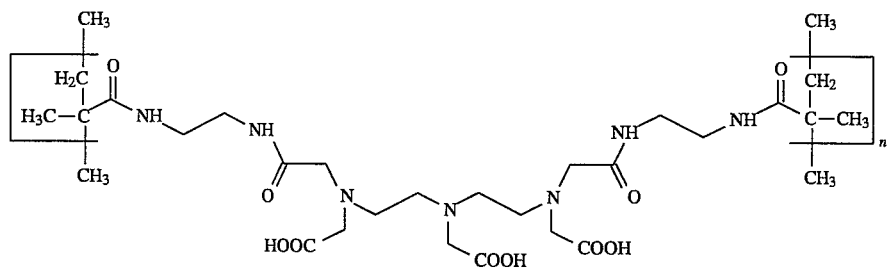

where $n \geq 2$.

A further aspect of the invention is the method of use of the above two recited compositions of matter, chelated with a paramagnetic metal ion as for enhancing the image formed by magnetic resonance techniques.

DETAILED DESCRIPTION OF THE INVENTION

The invention utilizes polymeric chelating agents represented below.

I. A magnetic resonance contrast enhancing agent comprising a chelating agent represented by the formula:

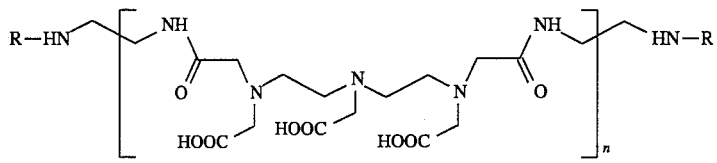

where $n \geq 2$, and R is selected from the group consisting of a polyamide co-polymer of an aminopolycarboxylate and diamine. The polyamide co-polymers of an aminopolycarboxylate includes compounds such as EDTA, DTPA and TTHA (triethylenetetraminehexaacetate), and the diamine includes compounds such as ethylenediamine, propylenediamine, and 1,3-diaminopropane.

II. A magnetic resonance contrast enhancing agent comprising a chelating agent represented by the formula:

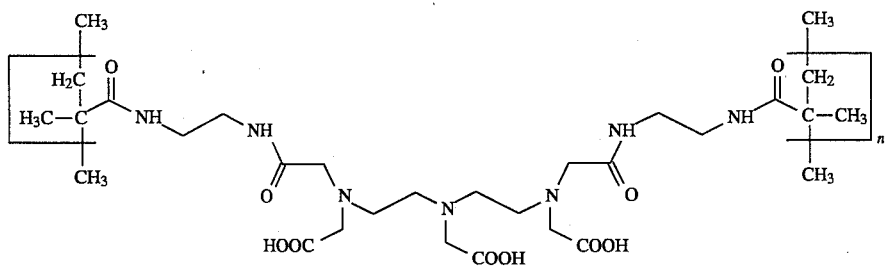

where $n \geq 2$.

These agents tenaciously bind metal ions and can be used to place otherwise toxic metal ions in organic environments, particularly biological environments by coordinating with the metal ion and thus preventing it from poisoning critical membranes or enzymes. The toxicity of the chelate is also lessened by having a metal bound to it as it will not remove essential metals from enzymes and membranes.

Metal ions easily bind to the chelate. Preferred metal ions include those having at least one unpaired electron, which is to say, those that are paramagnetic. Examples include Cr, Mn, Fe, Co, Tc and the lanthanide metals, particularly Gd, and Dy.

The metal complexes of the chelate can then be used as contrast enhancers for MR images. The method of administration of the complex, depends on the portion of the administration of the complex, depends on the portion of the anatomy to be imaged. For example, if the gastrointestinal tract is to be imaged, oral administration is preferred. For imaging of the liver, spleen, and kidneys, intravenous administration is preferred.

Various formulations of the metal chelate will have different physical properties. For example, highly crosslinked polymeric chelate will be fairly insoluble particles, but less highly cross linked polymers are more soluble. The clinician can use the various properties to his advantage. For example, if the area to be imaged includes delicate vascular systems, for example, the liver, or brain, a highly soluble form of metal chelate is preferred. If double contrast images of gastrointestinal tract are preferred, then more insoluble forms of metal chelate that coats the interior surface of the organs is preferred. Chelates with receptor molecules such as galactose will preferentially go to the liver.

A prior art open chain non-ionic MR contrast agent is DTPA-BMA, (OMNISCAN), U.S. Pat. No. 4,687,659, and has the following formula:

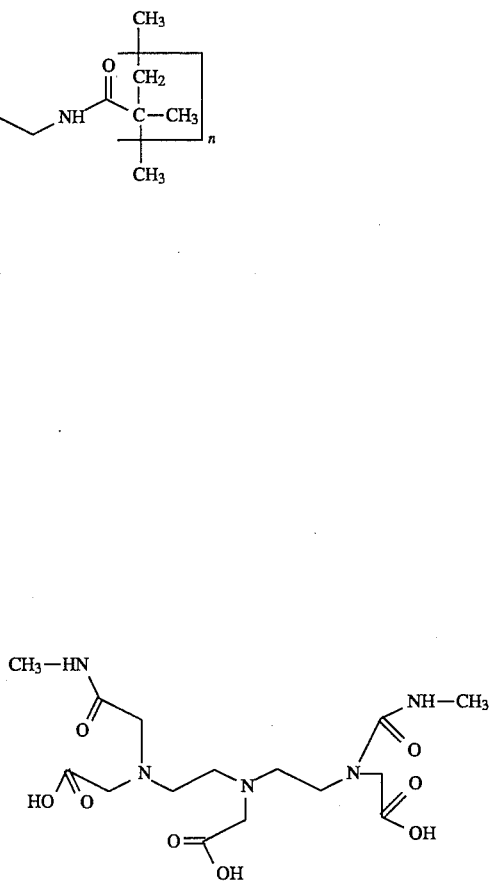

Another prior art non-ionic MR contrast agents is HP DO3A (PROHANCE), Inorganic Chemistry, 1991, 50, 1265, with the following formula:

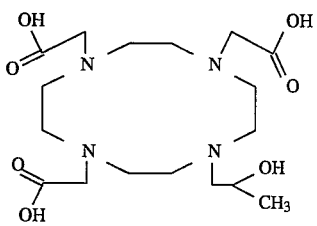

However, HPDO3A is expensive and difficult to synthesize. The more rigid ring structures improve GD-ligand stability but makes it more difficult to change groups to improve metal selectivity.

The polymeric compounds of the invention are confined to the intravascular region when injected into the circulatory systems. These agents are more stable than polymeric agents having ester linkages, and are hydrophilic. These compounds also have good coating properties and are useful for gastrointestinal images when taken orally. Examples 1 and 2 below set forth how these compounds are synthesized.

When used as magnetic resonance image enhancer, the chelate-metal complex may be formulated with an excipient, for example, unreacted saccharide, emulsifiers, solvents, such as saline solution, buffers, or the like, and may be added by methods well known in the art.

METHODS OF PREPARATION OF POLYMERIC CHELATING AGENTS

EXAMPLE 1 poly-(DTPA-ethylenediamide)

7.1 g of DTPA bisanhydride was taken in 150 ml of anhydrous DMF and 14 ml of triethylamine was added. Then 2.2 ml ethylenediamine dissolved 50 ml of anhydrous DMF was added slowly. With constant vigorous stirring under nitrogen, the mixture was stirred at room temperature for 30 minutes, then at 65° C. for 6 hours. The mixture was stirred overnight. Solvent was removed by evaporation under reduced pressure. The residue was dissolved in water and dialyzed in water for 48 hours. Then the product was isolated by precipitation with ethanol, and dried in a vacuum.

EXAMPLE 2

DTPA-ethylenediamine-methacrylate copolymer a) 10.7 g DTPA bisanhydride was added slowly with stirring to 100 ml of ethylenediamine. The mixture was heated at 60° C. for 1 hour and was stirred at room temperature for an additional 3 hours. Ethylenediamine was removed by evaporation under reduced pressure; it was then recrystallized from water-ethanol.

b) The diamide of DTPA (8.3 g) from step (a) was taken in 150 ml of anhydrous DMF and 10 ml of pyridine was added. Then 2.1 ml of methylmethacrylate was added and stirred overnight. The methanol produced in the reaction was removed by reflux.

50 mg of benzoylperoxide was added and the mixture was stirred at room temperature for 30 minutes under nitrogen. Then it was heated to 80° C. for 5 hours. Cooled, the solvent was removed by evaporation under reduced pressure. The product was taken into water and dialyzed for 48 hours and obtained by evaporating water under reduced pressure.

COMBINATION OF CHELATING AGENT WITH METAL IONS

EXAMPLE 3

Gadolinium (III) Chelates [Gd (III)]

The Gd(III) polymeric complexes of Examples 1 and 2 and gadolinium (III) chloride were each added in equimolar quantity to DTPA in water. The two mixtures were heated to 65° C. for two hours at pH 5.8. The reactions were monitored by testing for free gadolinium. The solvent from the reaction mixtures was removed by evaporation to dryness under reduced pressure. The residues were washed with ethanol and ether. Similarly, by substituting dysprosium chloride, iron chloride, chromium chloride, manganese chloride, cobalt chloride, or technetium pertechnetate in the presence of stannous ion for gadolinium chloride, one can obtain the respective metal chelates of these two compounds.

We claim:

1. A magnetic resonance contrast enhancing agent comprising a chelating agent represented by the formula:

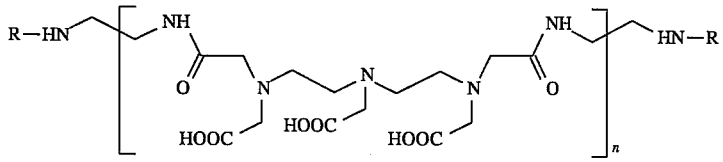

where n≧2, and R is selected from the group consisting of a polyamide co-polymer of an aminopolycarboxylate, and a diamine.

2. The composition of matter of claim 1, wherein said polyamide co-polymer of an aminopolycarboxylate is selected from the group consisting of EDTA, DTPA, and TTHA.

3. The composition of matter of claim 1, wherein said diamine is selected from the group consisting of ethylenediamine, propolylenediamine, and 1,3-diaminopropane.

4. A composition of matter comprising the chelating agent of claim 1, and a metal ion having at least one unpaired electron chelated to said chelating agent.

5. The compound of claim 4, wherein said metal ion is selected from the lanthanide group of metals.

6. The compound of claim 4, wherein said metal ion is Gadolinium.

7. The compound of claim 4, wherein said metal ion is selected from the group consisting of chromium, manganese, iron, cobalt and technetium.

8. A composition of matter comprising the chelating agent of claim 1 and an excipient for administration of a patient for magnetic resonance tomography.

9. A method of enhancing magnetic resonance contrast in a living subject, comprising administering internally to the subject an effective amount of a contrast agent which comprises the chelating agent of claim 1 and a metal ion of claim 5.

10. A method for using the composition of matter of claim 4 for imaging a patient, comprising the steps of:

administering the magnetic resonance contrast enhancing agent compound to a patient; and taking images of the patient.

11. A magnetic resonance contrast enhancing agent comprising a chelating agent represented by the formula:

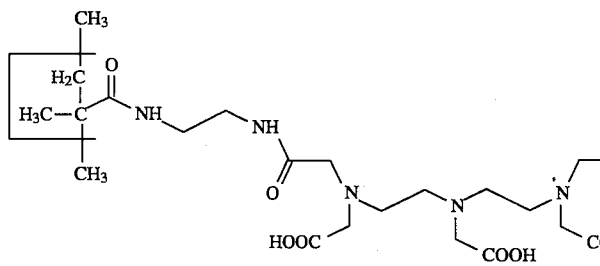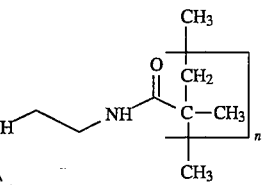

where $n \geq 2$.

12. A composition of matter comprising the chelating agent of claim 10, and a metal ion having at least one unpaired electron chelated to said chelating agent.

13. The compound of claim 12, wherein said metal ion is selected from the lanthanide group of metals.

14. The compound of claim 12, wherein said metal ion is Gadolinium.

15. The compound of claim 12, wherein said metal ion is selected from the group consisting of chromium, manganese, iron, cobalt and technetium.

16. A composition of matter comprising the chelating agent of claim 11 and an excipient for administration of a patient for magnetic resonance tomography.

17. A method of enhancing magnetic resonance contrast in a living subject, comprising administering internally to the subject an effective amount of a contrast agent which comprises the chelating agent of claim 11 and a metal ion of claim 13.

18. A method for using the composition of matter of claim 13 for imaging a patient, comprising the steps of:

administering the magnetic resonance contrast enhancing agent compound to a patient; and taking images of the patient.

* * * * *